(12) United States Patent
DeShazo et al.

(10) Patent No.: US 11,135,431 B2
(45) Date of Patent: Oct. 5, 2021

(54) IMPLANTABLE PULSE GENERATOR WITH MULTIPLE STIMULATION ENGINES

(71) Applicant: Advanced Neuromodulation Systems, Inc., Plano, TX (US)

(72) Inventors: Daran DeShazo, Lewisville, TX (US); Steven Boor, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 47 days.

(21) Appl. No.: 16/778,255

(22) Filed: Jan. 31, 2020

(65) Prior Publication Data
US 2021/0236822 A1    Aug. 5, 2021

(51) Int. Cl.
*A61N 1/36* (2006.01)
*A61N 1/378* (2006.01)
*A61N 1/372* (2006.01)

(52) U.S. Cl.
CPC ....... *A61N 1/36153* (2013.01); *A61N 1/3606* (2013.01); *A61N 1/378* (2013.01); *A61N 1/37235* (2013.01)

(58) Field of Classification Search
None
See application file for complete search history.

(56) References Cited

U.S. PATENT DOCUMENTS

| | | | |
|---|---|---|---|
| 2009/0259278 A1* | 10/2009 | Torgerson | A61N 1/36125 607/59 |
| 2011/0106213 A1* | 5/2011 | Davis | G16H 40/63 607/59 |
| 2013/0318259 A1* | 11/2013 | Sherman | G06F 13/28 710/25 |
| 2015/0224317 A1* | 8/2015 | Torgerson | A61N 1/36 607/62 |
| 2020/0147389 A1* | 5/2020 | Boor | A61N 1/36062 |
| 2020/0306533 A1* | 10/2020 | DeShazo | A61N 1/36157 |
| 2020/0306543 A1* | 10/2020 | Boor | A61N 1/37217 |
| 2020/0346005 A1* | 11/2020 | Boor | A61N 1/086 |

FOREIGN PATENT DOCUMENTS

WO    2018/136886 A1    7/2018

* cited by examiner

*Primary Examiner* — Brian T Gedeon
(74) *Attorney, Agent, or Firm* — Norton Rose Fulbright US LLP

(57) ABSTRACT

An implantable medical device (IMD) includes multiple stimulation engines for independently stimulating respective electrode sets of a lead system while avoiding collisions and/or channel contention during stimulation delivery. A first voltage multiplier is configured to generate an adjustable target voltage having sufficient headroom at an output node that is commonly coupled to anodic nodes of respective stimulation engines. Each stimulation engine includes a secondary voltage multiplier to drive the respective anode and a current regulator powered by a floating voltage supply, wherein the current regulator is coupled to a cathodic node and configured to control how much stimulation current is pulled from the patient tissue.

19 Claims, 10 Drawing Sheets

IMPLANTABLE PULSE GENERATOR WITH MULTIPLE STIMULATION ENGINES

TECHNICAL FIELD

The present disclosure generally relates to implantable pulse generators and stimulation circuitry used in association with neurostimulation systems (NS) including but not limited to spinal cord stimulation (SCS) systems.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more therapy delivery leads having a plurality of electrodes disposed in an area in which neurostimulation is desired. Alternatively, stimulation systems may comprise a micro-stimulation system In which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more multi-electrode leads. A typical RF system configuration comprises a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Whereas advances in IPG systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to IPG systems having multiple stimulation engines and associated power supply circuitry for independently stimulating respective electrode sets of a lead system having one or more implantable leads while avoiding collisions and/or channel contention during stimulation delivery. In one arrangement, a first voltage multiplier is configured to generate an adjustable target voltage having sufficient headroom at an output node that is commonly coupled to anodic nodes of respective stimulation engines. Each stimulation engine includes a secondary voltage multiplier to drive the respective anode and a current regulator powered by a floating voltage supply, wherein the current regulator is coupled to a cathodic node and configured to control how much stimulation current is pulled from the patient tissue.

In one aspect, an embodiment of the present patent disclosure is directed to an implantable medical device (IMD), which comprises, inter alia, a battery; a lead system comprising one or more leads configured to be positioned proximate to a patient's tissue, wherein each lead includes a plurality of electrodes; a first voltage multiplier configured to generate an adjustable target voltage at an output node based on a voltage supplied by the battery; and a plurality of stimulation engines, each configured to be individually optimized for delivering appropriate therapy to a select group of electrodes. Preferably, the stimulation engines are arranged to output optimized therapies to respective groups of electrodes simultaneously without the need for concern over stimulation delivery collisions—a collision being defined for purposes herein as when two or more stimulation patterns are delivered simultaneously but require different anode voltages. Example configurations therefore beneficially provide the ability to mitigate by preventing unintended current flow between different electrode sets or stimulation regions in a therapy application. In an example embodiment, each stimulation engine respectively includes a second voltage multiplier operative to drive an anodic node, a current regulator powered by a floating voltage supply, wherein the current regulator is coupled to a cathodic node, and the second voltage multiplier, the current regulator and the floating voltage supply are commonly referenced to a floating reference node. Each anodic node of the plurality of stimulation engines is commonly coupled to the output node of the first voltage multiplier. In one arrangement, a selector may be provided to selectively couple the anodic node and the cathodic node of a respective stimulation engine to a select portion of the electrodes for applying a select stimulation therapy to the patient's tissue according to a stimulation set. In one arrangement, the voltage multiplier of a respective stimulation engine is independently controlled by way of a respective digital control signal supplied by current regulation for optimizing a stimulation therapy delivered by the respective stimulation engine to a corresponding select portion of the electrodes. In one arrangement, the current regulator of a respective stimulation engine is configured to independently control cathodic currents drawn from the patient's tissue energized by the corresponding select portion of the electrodes. In one arrangement, the floating power supply of a respective stimulation engine comprises a charge pump capacitor charged to a battery voltage of the IMD.

In another aspect, an embodiment of the present patent disclosure is directed to a therapy system that includes an IMD comprising multiple stimulation engines as set forth above and an external programmer device for independently applying multiple stimulation therapies in a concurrent manner to respective portions of electrode loads by actuating suitable selector logic of the IMD according to respective stimulation sets, wherein at least one of stimulation delivery collisions and/or channel contention between the respective portions of electrodes is avoided during concurrent application of multiple stimulation therapies.

In another aspect, an embodiment of the present patent disclosure is directed to a stimulation therapy method using an IMD including a battery and a lead system of one or more leads configured to be positioned proximate to a patient's tissue, wherein each lead includes a plurality of electrodes. The example method comprises, inter alia, providing a first voltage multiplier configured to generate a range of target voltages at an output node based on a voltage supplied by the battery; and providing a plurality of stimulation engines (SEs), each respectively and independently powered by corresponding floating power supplies, wherein each SE is configured to support an anodic node and a cathodic node, the anodic node driven by a respective second voltage multiplier coupled to the output node of the first voltage multiplier and the cathodic node coupled to a respective current regulator powered by the corresponding floating power supply. The method further includes selectively coupling one or more sets of electrodes of the lead system to a corresponding number of SEs at respective anodic and cathodic nodes, and independently applying multiple stimulation therapies to respective sets of the electrodes wherein unintended current flow due to at least one of channel contention or electrical collision between the respective sets of electrodes of the lead system is avoided. Channel contention or electrical collisions can occur when multiple stimulation engines require simultaneous usage of one or more of the same electrodes, or when the multiple SEs would normally require different voltage multiplier settings at the same time.

Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment In this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
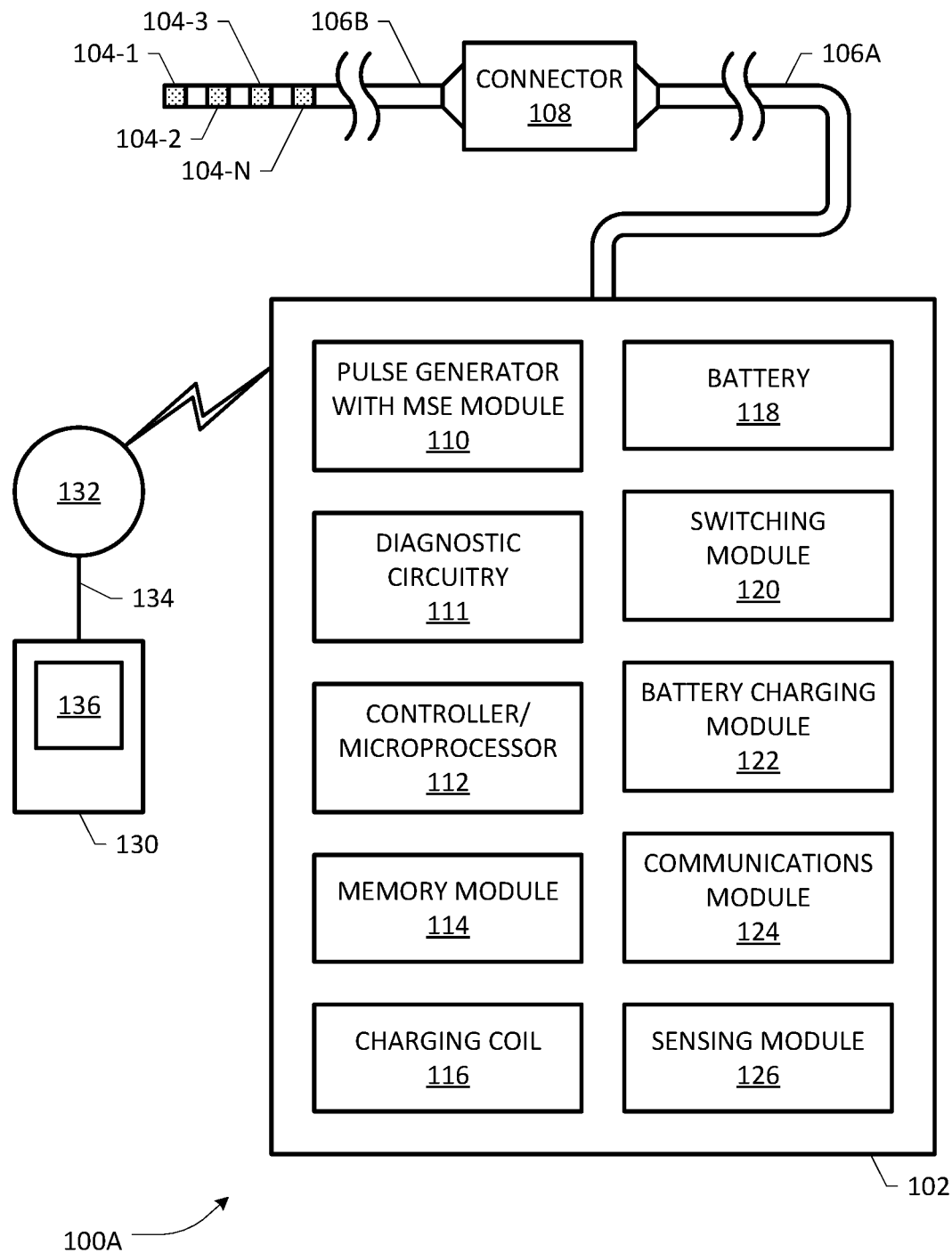
FIG. 1A depicts an example biostimulation system wherein an embodiment of an implantable medical device (IMD) with multiple stimulation engines of the present disclosure may be practiced according to the teachings herein.

In the description herein for embodiments of the present disclosure, numerous specific details are provided, such as examples of circuits, devices, components, and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) for generating electrical stimulation according to one or more multiple stimulation sets for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system 100A wherein an embodiment of an implantable medical device (IMD) with multiple stimulation engines of the present disclosure may be practiced according to the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A comprises an implantable pulse generator (IPG) or IMD 102 having a pulse generator portion including multiple stimulations engines adapted to provide independent therapies simultaneously without channel collision as will be set forth in additional detail further below. In one example embodiment, IMD 102 may be implemented as having a metallic housing or can that encloses a controller/processing block or module 112, pulse generating circuitry with multiple stimulation engine (MSE) module 110, a charging coil 116, a battery 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of IMD 102. Software/firmware code may be stored in memory 114, which may be integrated with the controller/processor module 112, and/or other suitable application-specific storage components (not particularly shown in this FIG.) for execution by the microcontroller or processor 112 and/or other programmable logic blocks to control the various components of IMD 102 for purposes of an embodiment of the present patent disclosure.

In one arrangement, IMD 102 may be coupled to a separate or an attached extension component 106A for providing electrical and physical connectivity to a lead system via a lead connector 108, wherein one or more leads each having a respective plurality of electrodes may be provided. By way of example, a single lead 106B is illustrated, wherein a distal end of the single lead 106B includes a plurality of electrodes 104-1 to 104-N. Where the extension component 106A is provided as a separate component, the extension component 106A may connect with a "header" portion of IPG/IMD 102 as is known in the art. If the extension component 106A is integrated with IMD 102, internal electrical connections may be made through respective conductive components. In general operation, electrical pulses are generated by the pulse generating circuitry 110 under the control of processing block 112, and are provided to the switching circuitry 120 that is operative to selectively connect to electrical outputs of the IMD, which are ultimately coupled to the electrodes 104-1 to 104-N at a distal end of the lead system 106B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may comprise one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (Ii) U.S. Patent Application Publication No. 2018/0008821, entitled, "IMPLANTABLE THIN FILM DEVICES", each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERING THE SAME", which is incorporated herein by reference.

In one arrangement, the lead system 106B (including extension 106A where provided) may comprise a lead body of insulative material encapsulating a plurality of conductors within the material that extend from a proximal end (that is proximate to IMD 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IMD 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur in some embodiments through the lead electrodes 104-1 to 104-N, corresponding conductors, and associated terminals. By way of illustration, an example embodiment of the stimulation system 100A may be provided with one or more leads, each having a plurality of lead electrodes 104-1 to 104-N comprising four electrodes, eight electrodes, etc., although any suitable number of electrodes (as well as corresponding conductive traces and terminals), wherein the leads may be configured to be positioned proximate to a patient's tissue at one or more locations for providing independent stimulation therapies according to the teachings herein. Additionally, alternatively, or optionally, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IMD 102, such as, e.g., processor and associated charge control circuitry for pulse generation, is described in U.S. Pat. No. 7,571,007, entitled "SYSTEMS AND METHODS FOR USE IN PULSE GENERATION", which is incorporated herein by reference. An example implementation of circuitry for recharging a rechargeable battery (e.g., battery charging circuitry 122) of an IMD using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", which is incorporated herein by reference. One or multiple sets of such circuitry may be provided for operation in association with respective current regulation circuitry as part of individual stimulation engines of module 110 for independently energizing different portions or sets of the electrodes of the lead system. In some example embodiments, different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Alternatively, multiple sets of such stimulation circuitry may be employed to provide high frequency pulse patterns (e.g., tonic stimulation waveform, burst stimulation waveform, and the like) that may include selective stimulation therapy treatments through one or more leads or electrodes 104-1 to 104-N as is also known in the art. Various sets of parameters may define the pulse characteristics and pulse timing for the pulses applied to the various lead electrodes as is known in the art. It should be appreciated that although constant current pulse generating circuitry is contemplated for some embodiments, any other suitable type of pulse generating circuitry may be employed in association with a multi-stimulation engine arrangement of the present invention.

In an example implementation of IMD 102, sensing circuitry 126 may be optionally provided, preferably adapted to measure a suitable electric parameter or transduced characteristic (e.g., voltage, current, capacitance, etc.) over a configurable or select time associated with the stimulation target or tissue through at least one of the electrodes proximate to the stimulation target. For example, the sensing circuitry 126 may measure an evoked compound activation potential (ECAP) waveform from an A$\beta$ sensory fiber or spinal cord. Optionally, the sensing circuitry 126 may store the measured/sensed electric data in memory 114. Furthermore, diagnostic circuitry 111 may be configured to intemperate with the sensing circuitry 126 and pulse generation and switching functionalities of IMD 102 for generating suitable diagnostic control signals that may be configured to adjustably control the operation of an MSE arrangement for purposes of the present invention as will set forth further below in additional detail.

An external device 130 may be implemented to charge/recharge the battery 118 of IMD 102 (although a separate recharging device could alternatively be employed), to access memory 114, and/or to program or reprogram IMD 102 with respect to the stimulation set parameters including pulsing specifications while implanted within the patient. In alternative embodiments, however, separate programmer devices may be employed for charging and/or programming IMD 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IMD 102. Optionally, in some embodiments, the wand 134 may comprise one or more temperature sensors for use during charging operations.

In general operation, a user (e.g., a doctor, a medical technician, or the patient) may initiate communication with IMD 102 by placing the wand 134 proximate to the stimulation system 100A. Preferably, the placement of the wand 134 allows the telemetry system to be aligned with the far-field and/or near field communication circuitry 124 of IMD 102. The external device 130 preferably provides one or more user interfaces 136 (e.g., touch screen, keyboard, mouse, buttons, scroll wheels or rollers, or the like), allowing the user to operate IMD 102. The external device 130 may be controlled by the user through the user interface 136, allowing the user to interact with IMD 102, including, e.g., effectuating programmatic control for dynamically configuring stimulation current pulses as well as independent selection/activation of different stimulation engines in some embodiments. Further, the user interface 136 may permit the user to move electrical stimulation along and/or across one or more of the lead(s) 106A/B using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, the user interface 136 may permit the user to designate which sets or subsets of electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally, some electrodes of the lead system 106/A/B may be configured to operate as current sink terminals or cathodes whereas other electrodes may be configured as current source terminals or anodes. Additionally or alternatively, the external device 130 may access or download the electrical measurements from the memory 114 acquired by the sensing circuitry 126.

In some embodiments, the external programmer device 130 may permit operation of IMD 102 according to one or more stimulation therapy programs or applications (e.g., an SCS application) to treat the patient. Each therapy program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulsing, monophasic pulsing, etc. IMD 102 may be configured to modify its internal parameters in response to the control signals from the external device 130 to vary the stimulation pulse characteristics of the respective stimulation therapies delivered by the multiple stimulation engines and transmitted through the selected portions of the electrodes of lead system 106A/106B to the tissue of the patient. Example stimsets and multi-stimset programs that may be used in association with one or more stimulation engines of the present invention may be found in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

Figure 1B:
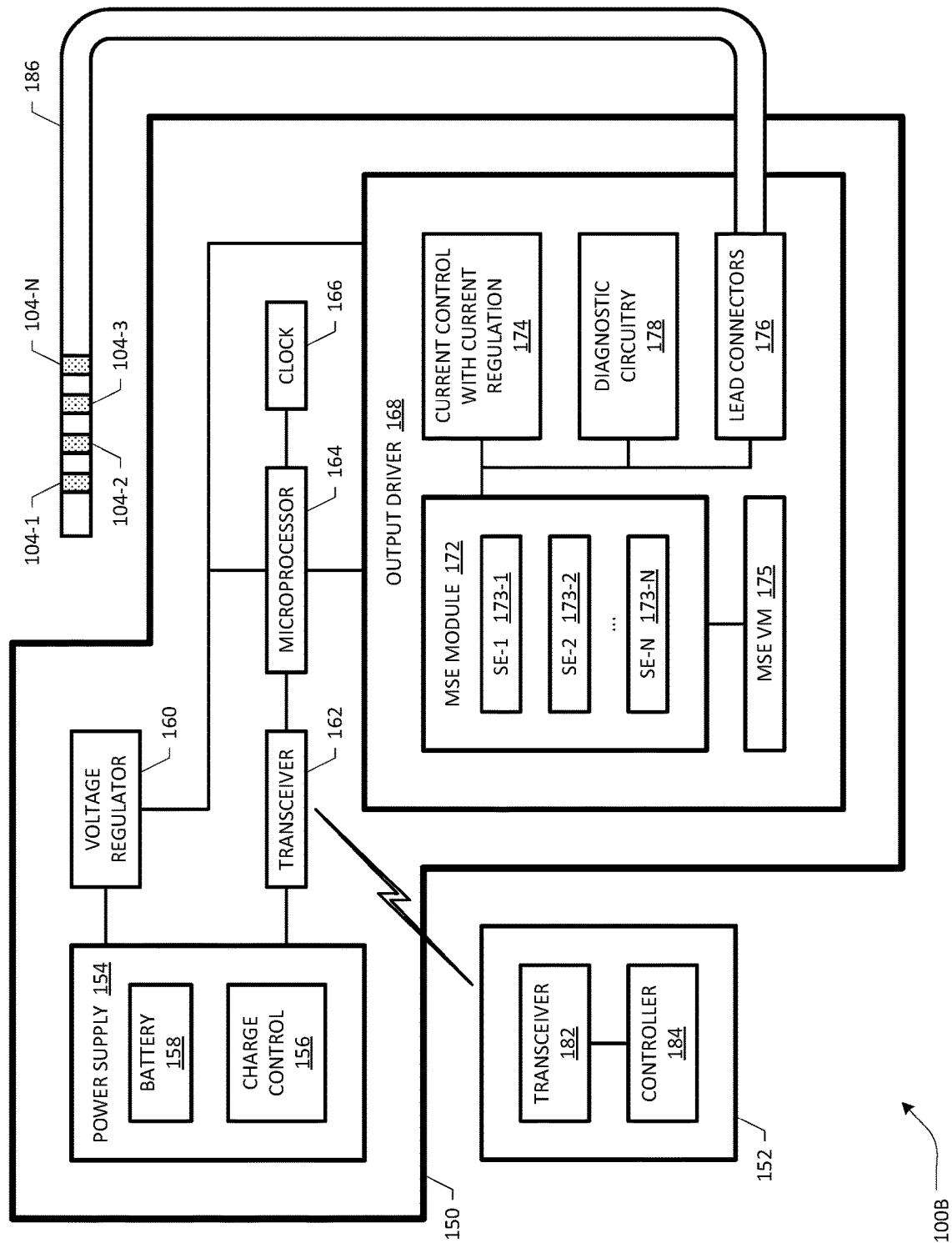
FIG. 1B depicts another view of a biostimulation system that illustrates additional details of an IMD's pulse generator including a plurality of stimulation engines for providing multiple stimulation therapies according to an embodiment of the present disclosure.

FIG. 1B depicts another embodiment of a biostimulation system 100B that illustrates additional details of an example IMD's pulse generator including a plurality of stimulation engines for simultaneously and/or selectively providing multiple stimulation therapies without channel collision or contention according to an embodiment of the present disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to the external device 130 described in the foregoing sections. IPG 150 may be implanted within the body of a human or animal patient (not shown) for providing electrical stimulation from IPG 150 to a selected area of the body via lead 186 under control of external programmer/controller 152. It should be appreciated that although lead 186 is illustrated to provide a stimulation portion of stimulation system 100B configured to provide stimulation remotely with respect to the generator portion 150 of stimulation system 100B, a lead as described herein is intended to encompass a variety of stimulation portion configurations including, e.g., a microstimulator electrode disposed adjacent to a generator portion.

Furthermore, although example lead systems 186 and 106A/B shown in FIGS. 1A/1B are exemplified as a single implantable lead, the teachings herein are not necessarily limited thereto. An example embodiment of the present invention may involve a lead system comprising two or more implantable leads, with each lead having a respective plurality of electrodes, wherein different combinations of electrodes/leads may be grouped into one or more channels in a stimulation therapy system. Stimulation current pulses according to different therapies may be applied by respective stimulation engines to different portions of electrodes according to a particular channel selection scheme regardless of whether one or more leads and/or one or more sets of electrodes are selected for stimulation.

IPG 150 may be configured as a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, microcontroller (or microprocessor) 164, clock 166, and output driver circuitry 168 comprising MSE module 172 having a plurality of stimulation engines (SEs) 173-1 to 173-N, each having respective current regulation circuitry, floating power supply, and an adjustable voltage multiplier, which will be described in further detail below. Alternatively or additionally, a separate current control/regulation block 174 along with a voltage multiplier may be provided in some embodiments for operation with MSE module 172. Further, suitable diagnostic circuitry 178 may also be provided as part of output driver 168 in some embodiments.

Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide recharging management with respect to battery 158. Transceiver 162 of an example embodiment of IPG 150 is operative to provide data/control communication between microprocessor 164 and a controller 184 of external programmer/controller 152, via transceiver 182 provided therewith. Transceiver 162 of an example embodiment, in addition to or in the alternative to providing data/control communication, may provide a conduit for delivering energy to power supply 154 via RF or inductive recharging as previously noted.

Microprocessor/controller 164 provides overall control with respect to the operation of IPG 150, such as in accordance with a program stored therein or provided thereto by external programmer/controller 152. One or more SEs 173-1 to 173-N of MSE module 172 may be configured to generate and deliver stimulation therapies having suitable pulse characteristics to selected sets or portions of electrodes 104-1 to 104-N under control of microcontroller 164. In general operation, for example, different SEs 173-1 to 173-N of MSE module 172 may be controlled to output optimized stimulation therapies simultaneously without collisions to different sets of electrodes selected under programmatic control. By way of illustration, a stimulation therapy may comprise delivering a constant current pulse of a desired magnitude/amplitude, duration, phase, and frequency to a tissue load present with respect to particular ones/sets of electrodes 104-1 to 104-N, which may be represented as respective lumped-element electrode/tissue interface (ETI) loads. Clock 166 preferably provides system timing information, such as may be used by microcontroller 164 in controlling system operation, as well as for different portions of MSE module 172 and/or voltage multiplier 175 in generating desired voltages, etc., described below in further detail.

Lead system 186 of the illustrated embodiment includes a lead body encapsulating a plurality of internal conductors coupled to lead connectors (not shown) to interface with lead connectors 176 of IPG 150 in a hermetically sealed arrangement. The internal conductors provide electrical connection from individual lead connectors to each of a corresponding one of electrodes 104-1 to 104-N, which may be configured to provide anodic current stimulation and/or cathodic current stimulation for application at, or proximate to, a spinal nerve or peripheral nerve, brain tissue, muscle, or other tissue depending on a desired therapy. As will be seen below, individual SEs 173-1 to 173-N may be configured to provide independently optimized stimulation current while delivering respective therapies simultaneously. Stated differently, example SEs 173-1 to 173-N may be independently controlled to output respective electrical signals by varying signal parameters such as intensity, duration and/or frequency in order to deliver a desired therapy and/or otherwise provide optimal stimulation current pulsing as described herein.

Skilled artisans will recognize that any number of electrodes, and corresponding conductors, may be utilized according to some embodiments, as previously noted. Moreover, various types, configurations and shapes of electrodes (and lead connectors) may be used according to some embodiments. An optional lumen (not shown) may extend through the lead 186, such as for use in delivery of chemicals or drugs or to accept a stylet during placement of the lead within the body of a patient. Additionally or alternatively, the lead system (stimulation portion) and IPG (generator portion) may comprise a unitary construction, such as that of a microstimulator configuration.

As mentioned above, programmer/controller 152 of an example embodiment provides data communication with IPG 150, such as to provide programmatic control, e.g., adjust stimulation settings, selection of SEs, selection and/or electrical polarity configuration of different groups of electrodes to which stimulation pulses are delivered, etc. An embodiment of a pulse generation system and the delivery of stimulation pulses that may be configured, mutatis mutandis, to interoperate with multiple SEs of the present patent disclosure may be found in U.S. Pat. No. 6,609,031, entitled "MULTIPROGRAMMABLE TISSUE STIMULATOR AND METHOD", which is incorporated by reference herein.

In one example embodiment of IPG 150, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to provide a regulated supply $V_{OUT}$ within a range acceptable to circuitry of IPG 150, including output driver circuitry 168 having MSE module 172, associated voltage multiplier 175 and/or current control and current regulation 174 for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too close to or below the $V_{OUT}$, causing the voltage regulator output voltage to also fall. In such a situation, therefore, the regulator can no longer provide the desired regulated output voltage. However, voltage regulator 160 of an embodiment may be adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control In association with suitable control signaling. For example, sensing circuitry, such as may utilize an analog-to-digital converter (ADC) in making voltage measurements may be utilized according to a preferred embodiment to provide information with respect to the battery voltage, which may be used by a digital control system (e.g., supported by microcontroller 164) in order to provide appropriate control signals e.g., select signals, for controlling the output voltage of voltage regulator 160. Additional details regarding voltage regulation may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), which is hereby incorporated herein by reference.

Skilled artisans will recognize that although an embodiment of voltage regulation is set forth hereinabove, a variety of techniques and circuits may be provided for operation with an IPG having multiple SEs described below In a particular implementation. Broadly, any suitable voltage regulator/multiplier arrangement may be adapted to provide a dynamic voltage adjustment to cover the voltage levels required for different stimulation currents under different loads according to some example embodiments of the present disclosure.

Figure 2:
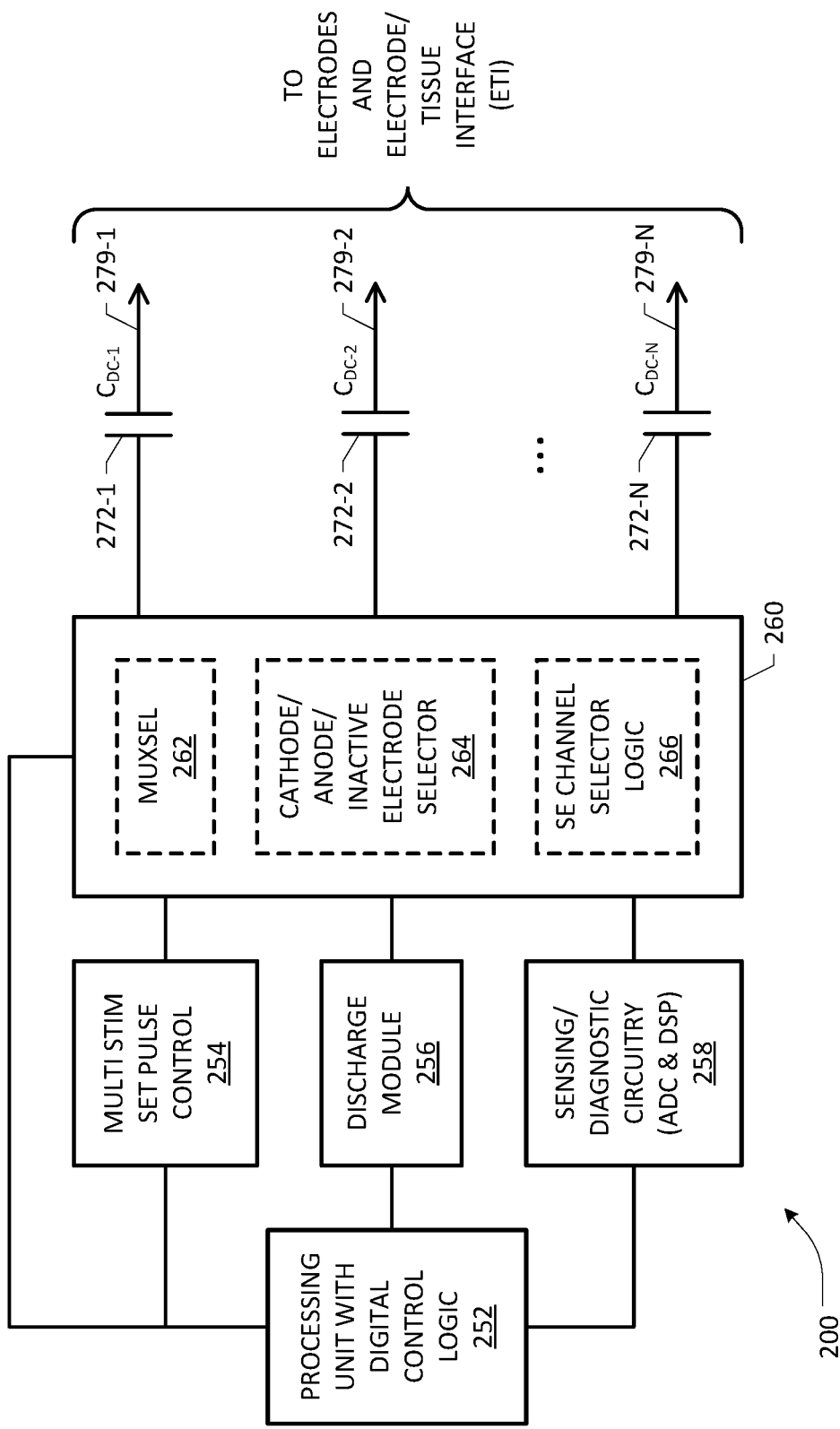
FIG. 2 depicts a block diagram of a pulse generator portion having multiple stimulation engine selection control and associated lead electrode arrangement according to an embodiment of the present disclosure.

FIG. 2 depicts a block diagram of a pulse generator portion 200 having multi-stimset pulse control, electrode and/or SE selection and configuration functionality and diagnostic circuitry, and associated lead electrode arrangement according to an embodiment of the present disclosure. One skilled in the art will recognize upon reference hereto that various functionalities associated with example blocks shown as part of the pulse generator portion 200 may be distributed and/or integrated among one or more blocks, subsystems and/or modules described hereinabove with respect to FIGS. 1A/1B. Consistent with the description provided previously, a processing unit 252 having or associated with suitable digital control logic is operatively coupled to multi SE control and multi-stim set pulse control 254, discharge module 256 and sensing/diagnostic circuitry 258 for facilitating various functionalities including but not limited to voltage measurements, active discharge cycling, electrode selection and configuration, SE selection, etc. under appropriate programmatic/diagnostics control. An input/output (I/O) interface block 260 is operatively coupled to a plurality of lead connectors 279-1 to 279-N interfaced with respective electrodes, which interfaces may be modeled as suitable lumped-element ETI circuit representations, wherein the lead connectors and associated electrodes may be configured as one or more leads, each having a respective plurality of electrodes. Regardless of the number of leads, a lead connector 279-1 to 279-N may be provided with a DC blocking stimulation capacitor ($C_{DC}$) for facilitating direct current flow blocking functionality with respect to the corresponding electrode that may be configured to operate as a stimulation node. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC-1}$ 272-1 is coupled to lead connector 279-1. Likewise, remaining lead connectors 279-N may be provided with respective $C_{DC-N}$ 272-N to facilitate DC blocking with respect to each corresponding lead electrode thereof.

Interface block 260 may include appropriate multiplexing and selection circuitry 262 and anode/cathode/inactive electrode selection circuitry 264 for measurement and sensing/diagnostics purposes wherein different electrodes of an electrode grouping of the lead system may be selectively configured for stimulation (e.g., anodic or cathodic stimulation), sensing, or designating unused/inactive states, etc., with appropriate electrical connections being made within an IPG device accordingly relative to the various components therein. In some embodiments, portions of diagnostic circuitry 258 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Additional details regarding configuring lead electrodes as cathodes or anodes, either during stimulation or for discharging, may be found in may be found in the '643 patent application publication incorporated by reference hereinabove. Still further, an SE selection block 266 may be provided for selectively coupling a (sub)set or portion of lead connectors to a select one of the plurality of SEs under programmatic control, which selection may be mediated via an external programmer (e.g., a clinician programmer or a patient controller) as previously noted.

Figure 3:
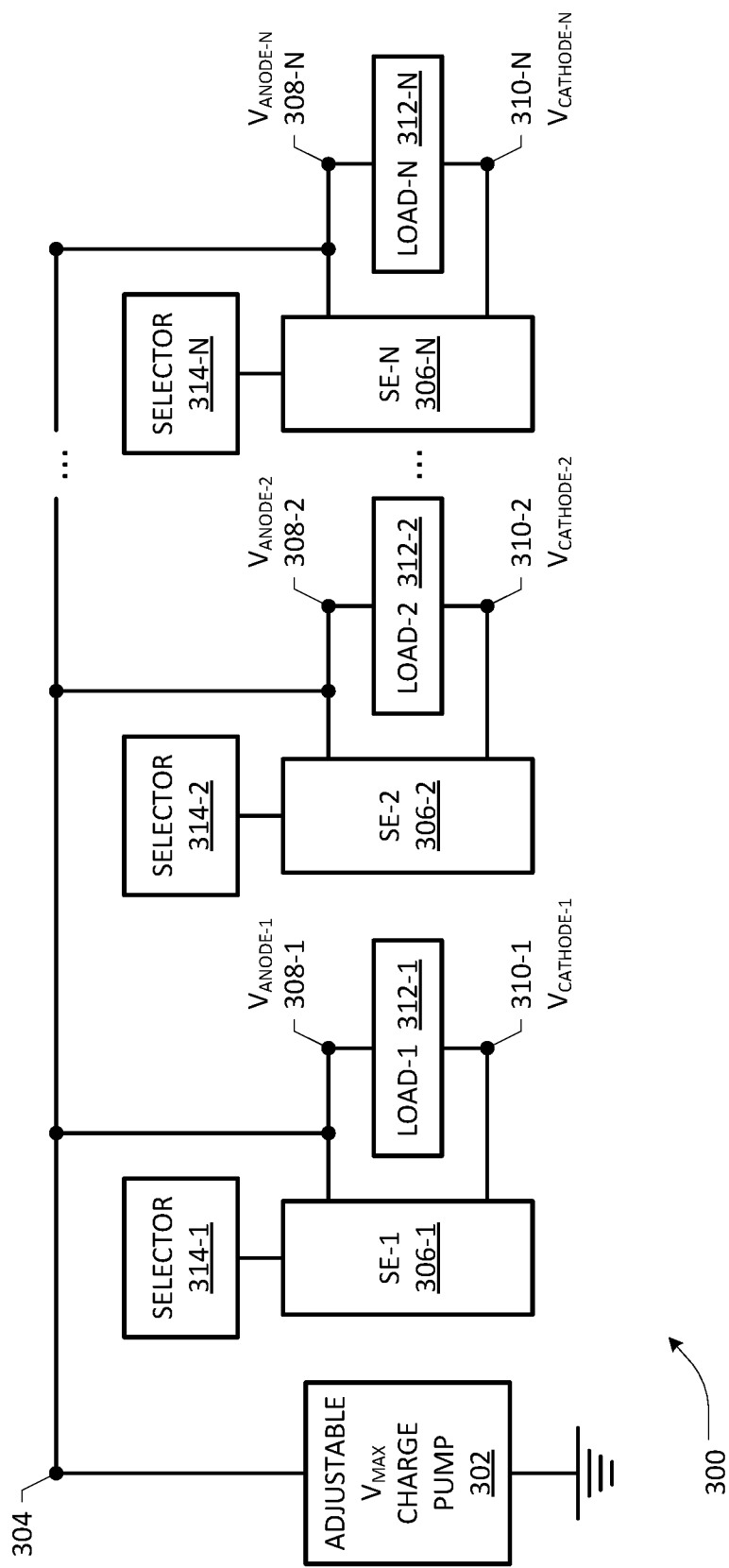
FIG. 3 depicts an example circuit arrangement having multiple stimulation engines that are powered from separate floating power supplies according to an embodiment of the present disclosure.

FIG. 3 depicts an example circuit arrangement 300 having multiple stimulation engines that may be powered from separate floating power supplies according to an embodiment of the present disclosure. An adjustable voltage multiplier 302 may be configured as a charge pump arrangement that can step up or step down from a regulated voltage supply, e.g., from a battery, to provide an output voltage that can cover up to a certain maximum voltage level ($V_{MAX}$) in order to support a sufficient voltage headroom (e.g., 12.0V to 20.0V) for different stimulation settings applicable for a therapy application. For example, a DRG application may require a lower $V_{MAX}$ level than an SCS or DBS application. In one arrangement, VM charge pump 302 may be implemented as a stacked charge pump capacitor arrangement to provide different output voltages at an output node 304. In general, $V_{MAX}$ charge pump 302 may be configured to operate as a primary voltage supply that may be commonly used by different SEs 306-1 to 306-N to apply stimulation to respective sets of electrodes of a lead system. As illustrated, a plurality of loads 312-1 to 312-N, each representing a respective set of electrodes, are coupled between an anodic node ($V_{ANODE}$) and a cathodic node ($V_{CATHODE}$) of a respective SE. In some embodiments, each SE may be provided with a selector logic module for selectively coupling and/or energizing a select set or portion of the electrodes as the respective load therefor. As shown in FIG. 3, selector logic modules 314-1 to 314-N are operative with respect to corresponding SE modules 306-1 to 306-N. In some embodiments, the overall selection logic functionality may be centrally or commonly provided with respect to all SE modules 306-1 to 306N as part of an IMD's I/O interface block.

Figure 4:
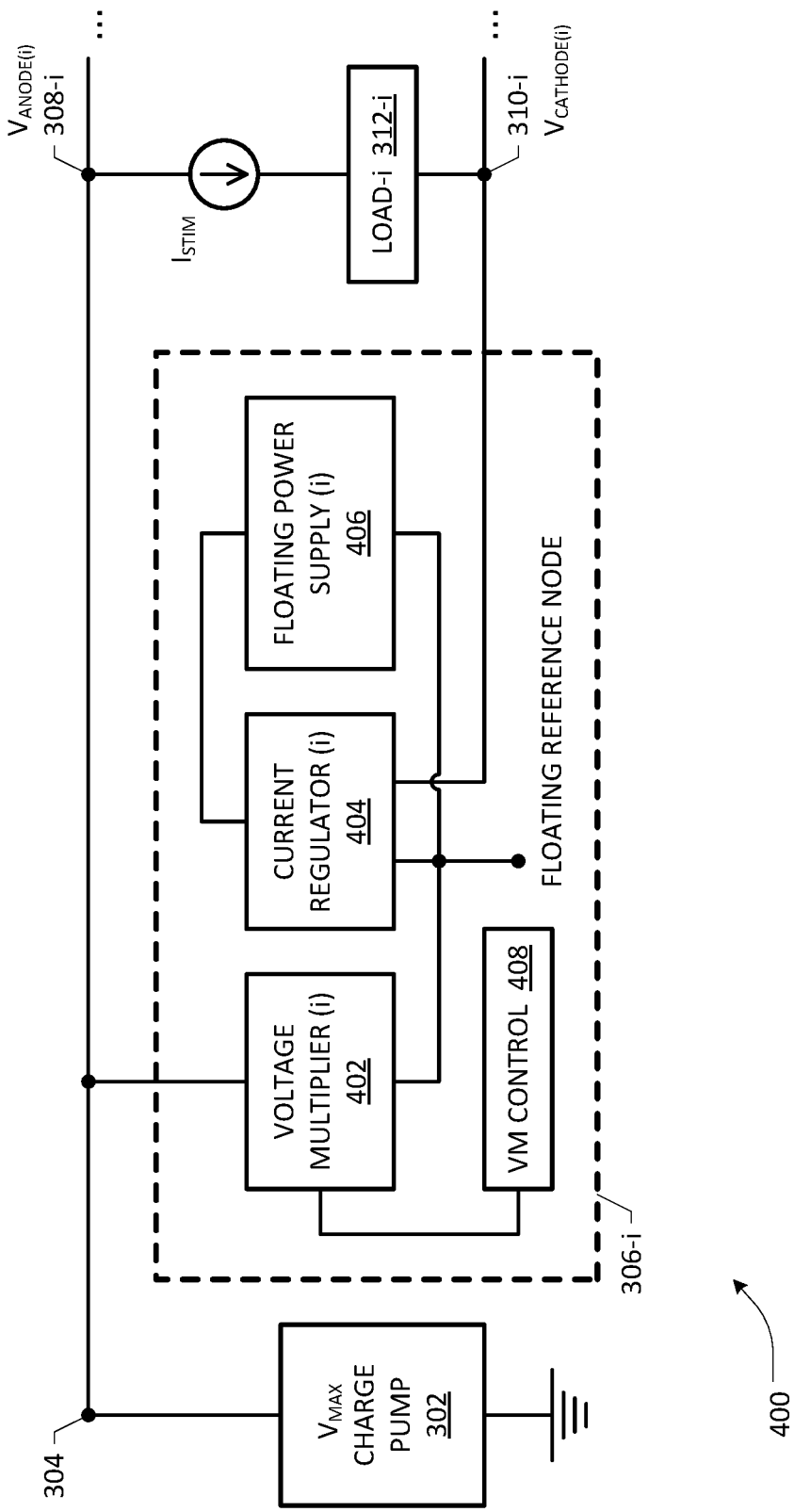
FIG. 4 depicts an example stimulation engine with additional details that may be implemented in multiple instances in an embodiment of the circuit arrangement of FIG. 3.

FIG. 4 depicts a circuit portion 400 of the arrangement 300, wherein an example stimulation engine is shown with additional details that may be implemented in multiple instances according to an embodiment of the present invention. Each stimulation engine 306-i respectively includes a voltage multiplier 402, a current regulator 404, and a "floating" power supply 406, in addition having independent control 408 for controlling voltage multiplier 402. In one arrangement, voltage multiplier 402 and power supply 406 may each be implemented as stacked charge pump capacitor arrangements specifically configured for respective functionalities. Voltage multiplier 402 is configured to drive a current source path coupled to respective anodic node 308-i of the respective stimulation engine 306-i, wherein each anodic node is commonly coupled to the output node 304 of $V_{MAX}$ charge pump 302. In one arrangement, the circuitry $V_{MAX}$ charge pump 302 may be referenced to a known ground, e.g., a ground terminal associated with the IMD's battery. The circuitry comprising the different constituent components of each stimulation engine 306-i may be referenced to a floating reference node, wherein respective current regulator 404 is powered by power supply 406 and configured to draw a stimulation current ($I_{STIM}$) flowing through a respective load 312-i (e.g., as a cathodic current pulled from the patient's tissue energized by the corresponding select set of electrodes under a constant current stimulation therapy). In one arrangement, $V_{MAX}$ charge pump 302 may be referred to as a primary or first voltage multiplier and voltage multiplier 402 of each stimulation engine 306-1 may be referred to as a secondary or second voltage multiplier.

It should be appreciated that because each stimulation engine 306-i is operated with its own floating power supply 406, wherein a respective secondary voltage multiplier 402 is independently controlled and a respective current regulator 404 is independently controlled with respect to how cathodic currents are pulled from the patient's tissue, a respective stimulation engine 306-i may be independently optimized for stimulation delivery efficiency in a particular therapy application. In one arrangement, $V_{MAX}$ charge pump 302 may be provided by a relatively small charge pump capacitor that allows all anodic electrodes 308- to be connected together at output node 304 that operates as a common voltage reference to the human tissue, thereby avoiding current flow between different SE paths. As there is no current flow between the different SE paths, respective voltage multipliers 402 can be independently optimized for stimulation efficiency. As such, $V_{MAX}$ charge pump 302 may not need to delivery any appreciable current, since all stimulation delivery currents and all stimulation circuitry currents are provided respectively by the voltage multipliers 402 and floating power supplies 406. In an example arrangement, floating power supplies 406 may be configured as respective charge pump capacitors charged to the IMD battery voltage.

As the respective stimulation engines 306-i have electrically isolated stimulation current paths, it becomes virtually impossible in an example arrangement 300 of the present invention for stimulation delivery collisions to occur regardless of how or how many channel/electrode configurations are implemented in a therapy application. Accordingly, an added advantage of the present invention is that in one embodiment each stimulation engine 306-1 may be programmed and controlled in a relatively straightforward manner without having to resort to complex collision avoidance algorithmic control, which is a significant issue in the state of the art IPG implementations as discussed elsewhere in the present patent application.

Figure 5:
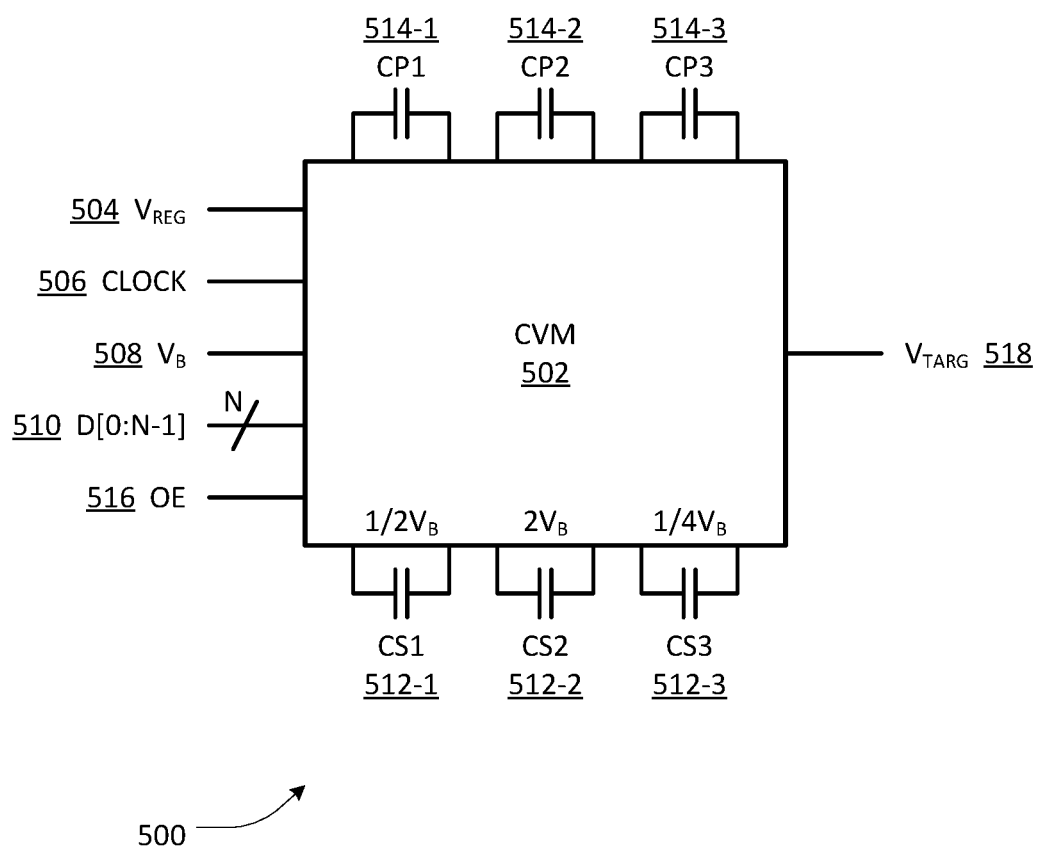
FIG. 5 depicts a high-level block diagram of an adjustable voltage multiplier that may be used in different configurations in an embodiment of the circuit arrangement of FIG. 3 for purposes of the present disclosure.

FIG. 5 depicts a high-level block diagram of an adjustable voltage multiplier that may be used in different configurations in an embodiment of the circuit arrangements of FIGS. 3 and/or 4 for purposes of the present disclosure. By way of illustration, voltage multiplier 500 may be configured as an adjustable charge pump arrangement operative to generate a target voltage at an output node for purposes of an example embodiment of the present disclosure. Generally, a representative embodiment of voltage multiplier configuration 500 may be arranged to support power supply voltage multiplier and/or divider elements in a binary ladder distribution to provide a desired number of output voltage steps using a circuit design which may readily be implemented in a single integrated circuit (IC) or multiple ICs. For example, a capacitive voltage multiplier (CVM) provided according to a representative embodiment may be operative as a DC-to-DC voltage conversion system comprising a voltage doubler generating twice the battery voltage, the battery itself generating the battery voltage, a voltage halver generating half of the battery voltage, and a voltage quarterer generating a quarter of the battery voltage, and/or any other fractional/ multiples thereof. Accordingly, circuitry of an example voltage multiplier configuration may preferably operate to combine the different voltages to provide a range of output voltages in multiple steps, e.g., one-quarter battery voltage (¼ $V_{BATT}$ or $V_B$), or other power source voltage steps. By using such different sources in various combinations and/or by "stacking" these different sources in various ways, the voltage multiplier circuit may be used to provide desired voltages over a suitable range. For example, the output voltage of such a voltage multiplier may range from ¼ $V_B$ to 3¾ $V_B$, in one-quarter battery voltage steps in an example implementation.

In FIG. 5, configuration 500 of the illustrated embodiment includes CVM circuitry block 502 implemented as an IC or other monolithic chip device, a first plurality of pump capacitors CP1 514-1, CP2 514-2, and CP3 514-3, and a second plurality of storage capacitors CS1 512-1, CS2 512-2, and CS3 512-3. CVM 502 is preferably operative responsive to signal inputs $V_{REG}$ 504, CLOCK 506, $V_B$ 508, an N-bit control signal 510, (e.g., a 4-bit signal that may be generated, controlled and/or otherwise configured by a suitable digital control block) and an output enable (OE) signal 516, in order to generate a target output voltage ($V_{TARG}$) at an output node or pin 518.

$V_{REG}$ 504 of the illustrated embodiment provides a regulated voltage input for use by circuits (e.g., digital control circuits) of CVM 502 in providing voltage multiplication. In an example implementation, $V_{REG}$ 504 is typically at a logic level (e.g., 2.2 volts) that is lower than the power supply voltage (e.g., $V_B$ 508). CLOCK 506 is a system clock signal used for synchronizing operation of aspects of CVM 502 with operation of aspects of a host system (e.g., IMD/IPG of a biostimulation system), such as for digital communication, voltage output timing, etc. $V_B$ 508 provides a power supply voltage level input for use in voltage fractional multiplication by CVM 502. For example, $V_B$ 508 may provide unregulated battery voltage input, such as 4.1 volts where a lithium-ion battery is used. Digital control 510 provides a suitable digital input signal, which may be used in the illustrated embodiment for selecting a desired output voltage level, e.g., depending on whether CVM 502 is used as a primary or secondary VM, or a floating power supply of an MSE module of the present invention. OE 516 is operative to selectively enable the output voltage ($V_{TARG}$) at output node 518. Accordingly, a signal provided at OE 516 may comprise a binary logic level signal which may be asserted at appropriate times (e.g., depending on the CLOCK signal 506).

Pump capacitors CP1 514-1, CP2 514-2, and CP3 514-3 of the illustrated embodiment may be utilized in a voltage generation cycle. Because of the use of a partitioned circuit configuration of CVM 502 of a representative embodiment (and due to the relatively low voltages experienced by capacitors CP1 514-1, CP2 514-2, and CP3 514-3 in an example implementation), the pump capacitors may be relatively small, such as on the order of 0.5 µF. One or more storage capacitors CS1 512-1, CS2 512-2, and CS3 512-3 may be configurably stacked in providing a desired output voltage ($V_{TARG}$). Moreover, in order to sustain a relatively constant (i.e., flat) output voltage level during a voltage output cycle, storage capacitors CS1 512-1, CS2 512-2, and CS3 512-3 may be larger than the pump capacitors, such as on the order of 100 µF. Accordingly, various capacitors utilized in generating a particular voltage multiple or voltage fraction need not be matched in implementing a particular charge pump arrangement of CVM 502. For example, according to a representative embodiment where pump capacitors are used in combination with storage capacitors to generate a voltage multiple or voltage fraction, the capacitors are not necessarily matched.

It should be appreciated that through controlled stacking of the various storage capacitors in providing a desired output voltage, the maximum voltage levels experienced by particular capacitors (and other components) may be minimized. Therefore, one or more of the capacitors or other circuitry may be sized differently with respect to one another according to some embodiments. Accordingly, various ones of the pump capacitors may be sized differently with respect to other pump capacitors and/or various ones of the storage capacitors may be sized differently with respect to other storage capacitors. Skilled artisans will therefore recognize that various charge pump capacitor configurations may be implemented in additional or alternative embodiments for purposes of the present patent disclosure.

In operation according to a representative embodiment, CVM 502 provides selectable voltage output at $V_{TARG}$ node 518 in various increments, e.g., from $0V_B$ to $3\frac{3}{4} V_B$ in $\frac{1}{4} V_B$ steps. In one implementation, a logic low input at OE 516 may be used to turn the voltage output at $V_{TARG}$ node 518 off (i.e., 0 $V_B$), such as during a voltage generation or refresh cycle. A logic high input at OE 516 in combination with a particular N-bit combination logic input at terminal 510 may be used to turn the voltage output at $V_{TARG}$ node 518 on and select a particular voltage level from $\frac{1}{4} V_B$ to $3\frac{3}{4} V_B$ by appropriately configuring at least a portion of the charge pump capacitors. Other fractional voltages may be provided through the use of combinations of capacitors different than those of the exemplary embodiment shown in FIG. 5.

Generation of voltages using a voltage multiplier/conversion circuit such as the representative circuit 500 shown in FIG. 5 may include a plurality of phases, wherein an output of the voltage multiplier/conversion circuit may be disabled during one or more such phases. For example, a charge phase may be used to charge the pump capacitors with current from the power supply and a pump phase may be used to transfer the charge into storage capacitors (the combination of these phases being referred to as a generation phase). A source phase may be used to output a desired voltage using an appropriate configuration of pump capacitors and/or storage capacitors (i.e., charge pump capacitors) based on the digital control logic signals 510. For example, respective voltage multipliers 402 of stimulation engines 306-$i$ may be independently controlled by applying suitable digital control logic signals 510, which may be generated in conjunction with and/or responsive to the current regulation required for energizing a particular load configuration. Additional details regarding example interconnection or configuration of pump and storage capacitors in a charge phase and a pump phase, as well as selection of different output voltages ($V_{TARG}$) using appropriate selection circuitry operating under suitable digital control may be found in U.S. Pat. No. 8,446,212, entitled "PULSE GENERATOR HAVING AN EFFICIENT FRACTIONAL VOLTAGE CONVERTER AND METHOD OF USE", which is incorporated herein by reference.

Figure 6:
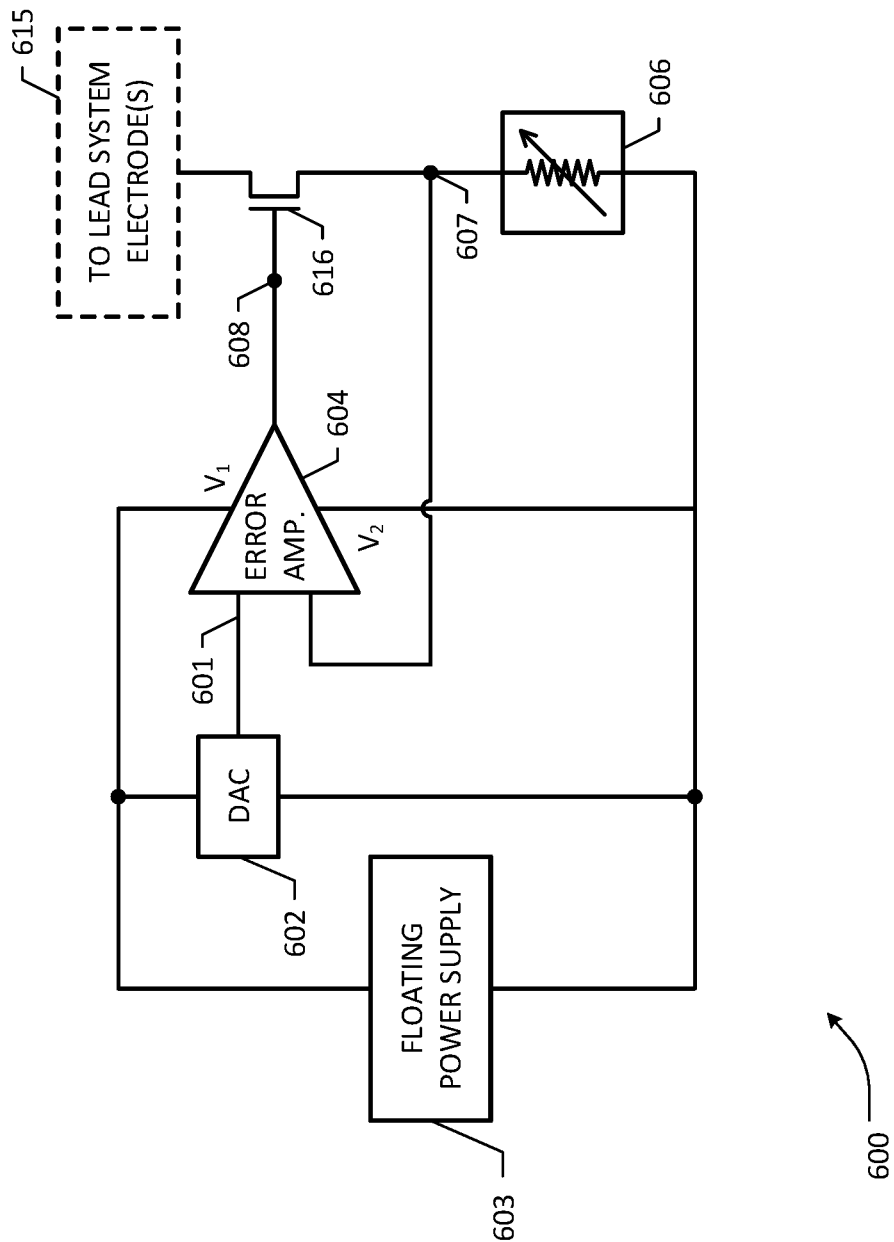
FIG. 6 depicts a block diagram of a current regulator that may be implemented as part of a stimulation engine for use in the circuit arrangement of FIG. 3 according to an embodiment of the present disclosure.

FIG. 6 depicts a block diagram of an example current regulator 600 that may be implemented as part of a stimulation engine for use in the circuit arrangement of FIGS. 3 and/or 4 according to an embodiment of the present disclosure. A digital-to-analog converter (DAC) 602 may be provided to interface with appropriate voltage supply (e.g., having suitable magnitude and polarity, depending on the type of stimulation current being programmed) to generate a digitally-programmed analog voltage level as an output signal 601, which may be provided to an error amplifier 604 having one or more power supply rail voltages driven by a floating power supply 603. In one arrangement, the error amplifier 604 may be implemented as an op amp having two inputs for providing a differential input and operative with a pair of power supply rail voltage nodes, $V_1$ and $V_2$, of power supply 603 (where $V_B = |V_1 - V_2|$), which is also connected to DAC 602. In some arrangements, $V_1$ and $V_2$ nodes may be selectively biased depending on whether cathodic stimulation current or anodic stimulation current is being programmed. Regardless of whether anodic or cathodic stimulation is programmed, the digitally-programmed analog voltage signal output (VDAC) 601 may be coupled to a first input of the error amplifier 604, wherein a second input is coupled to a programmable resistor network 606 operative to provide a digitally-programmed resistance (RSCALE) in a feedback loop arrangement for modulating or otherwise adjusting a stimulation current output. In general operation, the error amplifier 604 may be programmatically configured to generate a desired amount of stimulation current ($I_{STIM}$), which may be set by the application of Ohm's Law in view of the digitally-programmed resistance RSCALE, where $I_{STIM} = (VDAC/RSCALE)$, at a node 607 to which the programmable resistor network 606 is connected.

In one arrangement, a current conducting device 616 may be coupled to the node 607 for facilitating the stimulation current $I_{STIM}$ flowing through one or more lead system electrodes, generally shown at reference numeral 615. Device 616 may be controlled by an output node 608 of error amplifier 604. Although not shown herein, a differential input comparator may be configured to receive the error amplifier signal at node 608 as an input for comparison with a power supply rail voltage provided as an input in order to generate an output signal, which may be provided as a CVM control signal operative to actuate a digital counter. Additional details regarding CVM control in conjunction with current regulation of an IPG may be found in U.S. patent application Ser. No. 16/520,052, entitled, "CAPACITIVE VOLTAGE MULTIPLIER FOR PROVIDING ADJUSTABLE CONTROL DURING A STIMULATION PULSE", incorporated by reference herein, which may be modified, mutatis mutandis, for application in an MSE configuration in some example embodiments of the present patent disclosure.

Figure 7:
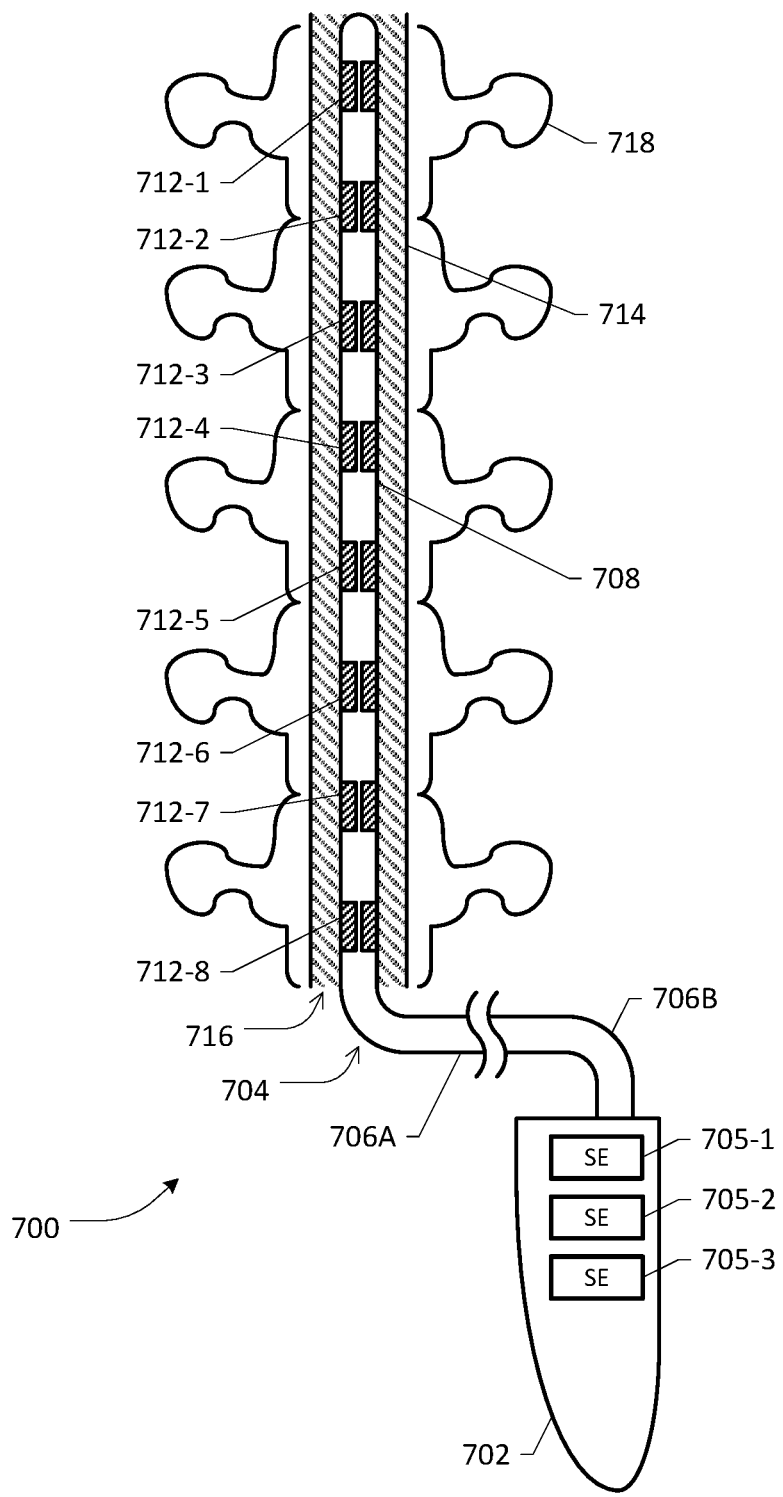
FIG. 7 illustrates an example spinal cord stimulation (SCS) therapy application involving an IMD with multiple stimulation engines and associated lead system having a plurality of electrodes that may be stimulated using multiple stimulation sets without channel collision according to an embodiment of the present disclosure.

FIG. 7 illustrates an example spinal cord stimulation (SCS) therapy application 700 involving a pulse generator or IMD 702 and associated lead system 704 having a plurality of electrodes 712-1 to 712-8 wherein different groupings of electrodes may be simultaneously and independently energized pursuant to respective stimset programs during a stimulation therapy according to an embodiment of the present disclosure. Preferably, the lead system 704 comprises a lead body 706A/B coupled to an implantable lead 708 that may be positioned at a desired target position in an epidural space 716 defined by a plurality of vertebrae of a patient so as to be in close proximity to a nerve tissue of interest, e.g., a spinal cord 714. Example implantable lead 708 includes eight electrodes 712-1 to 712-8, which may comprise ring electrodes, segmented or split electrodes, and the like that may be separated from one another by equal or unequal portions of encapsulating material. The implantable lead 708 is connected via lead body 706A/706B to IPG/IMD 702 that includes at least an embodiment of an MSE module of the present disclosure that may be configured to be operative with suitable diagnostic circuitry and/or programming devices. By way of example, three SEs 705-1, 705-2, 705-3 are shown, which may be selectively and independently configured to provide different combinations of stimulation therapy to electrodes 712-1 to 712-8. Illustratively, SE 705-1 may be activated to stimulate electrodes 712-1 to 712-4 and SE 705-2 may be activated stimulate electrodes 712-5 to 712-8, while SE 705-3 may be inactive. Accordingly, electrodes 712-1 to 712-4 and electrodes 712-5 to 712-8 may be energized, i.e., stimulated, e.g., with appropriate constant current pulses, wherein the individual stimulation currents drawn via respective loads may be optimized based on respective SE control as previously described.

Figure 8:
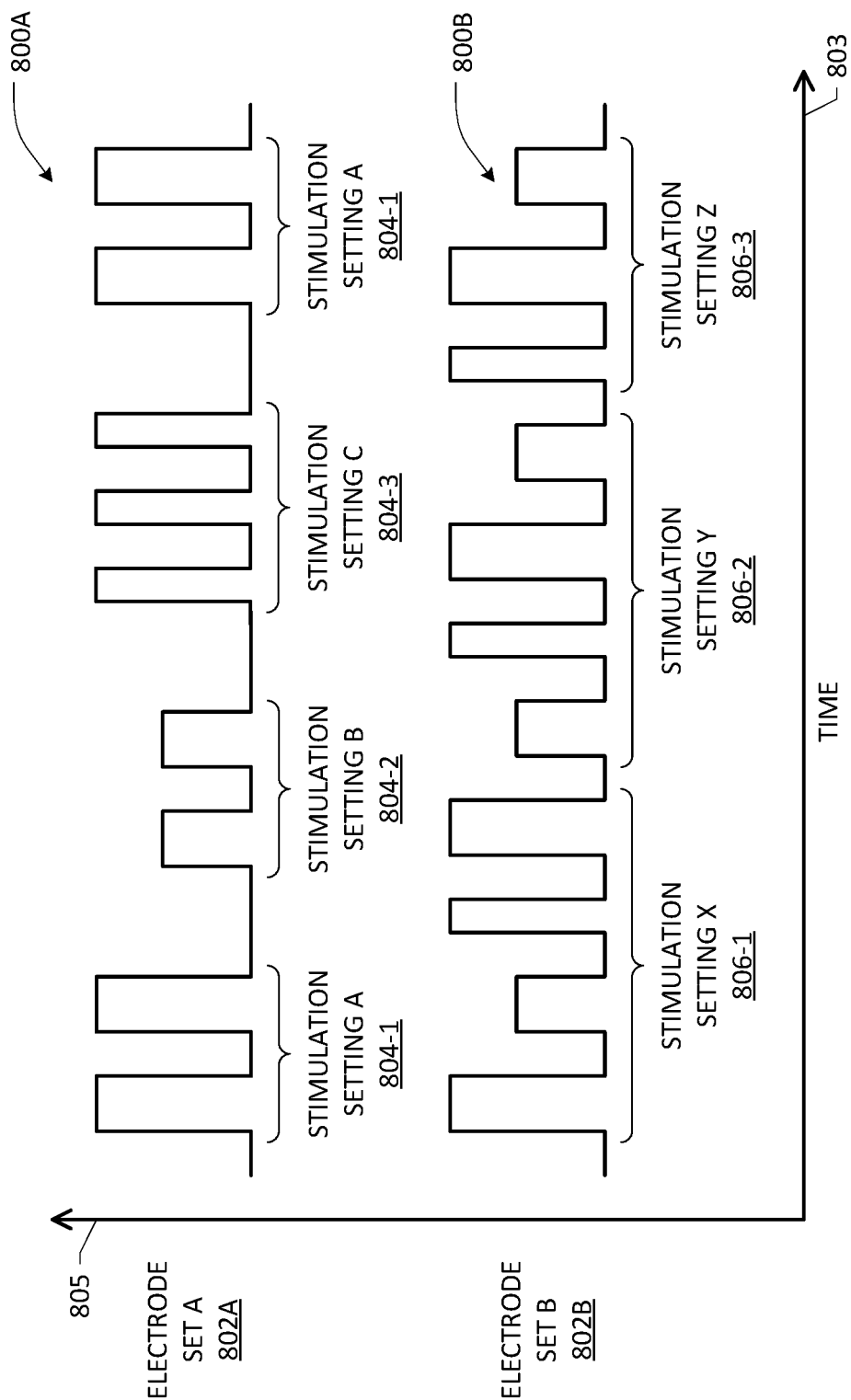
FIG. 8 depicts a panel of illustrative waveforms associated with stimulation therapy patterns applied to two sets of electrodes according to some embodiments of the present disclosure.

FIG. 8 depicts a panel of illustrative waveforms associated with stimulation therapy patterns applied to two sets of electrodes according to some embodiments of the present disclosure. Panels 800A and 800B exemplify stimulation waveforms respectively associated with two electrode sets 802A 802B, each energized by a respective stimulation engine, wherein an electrical parameter (e.g., current amplitude) and time are plotted on Y-axis 805 and X-axis 803, respectively, as shown. Waveform panel 800A is illustrated as a plurality of stimulation settings 804-1 to 804-3 that are applied successively over time to electrode set A 802A. Likewise, waveform panel 800B is illustrative of a plurality of stimulation settings 806-1 to 806-3 applied to electrode set B 802B. Although both waveforms overlap temporally, there is no unintended stimulation collision because of the independent VM control and current regulation provided in accordance with the teachings herein.

Figure 9:
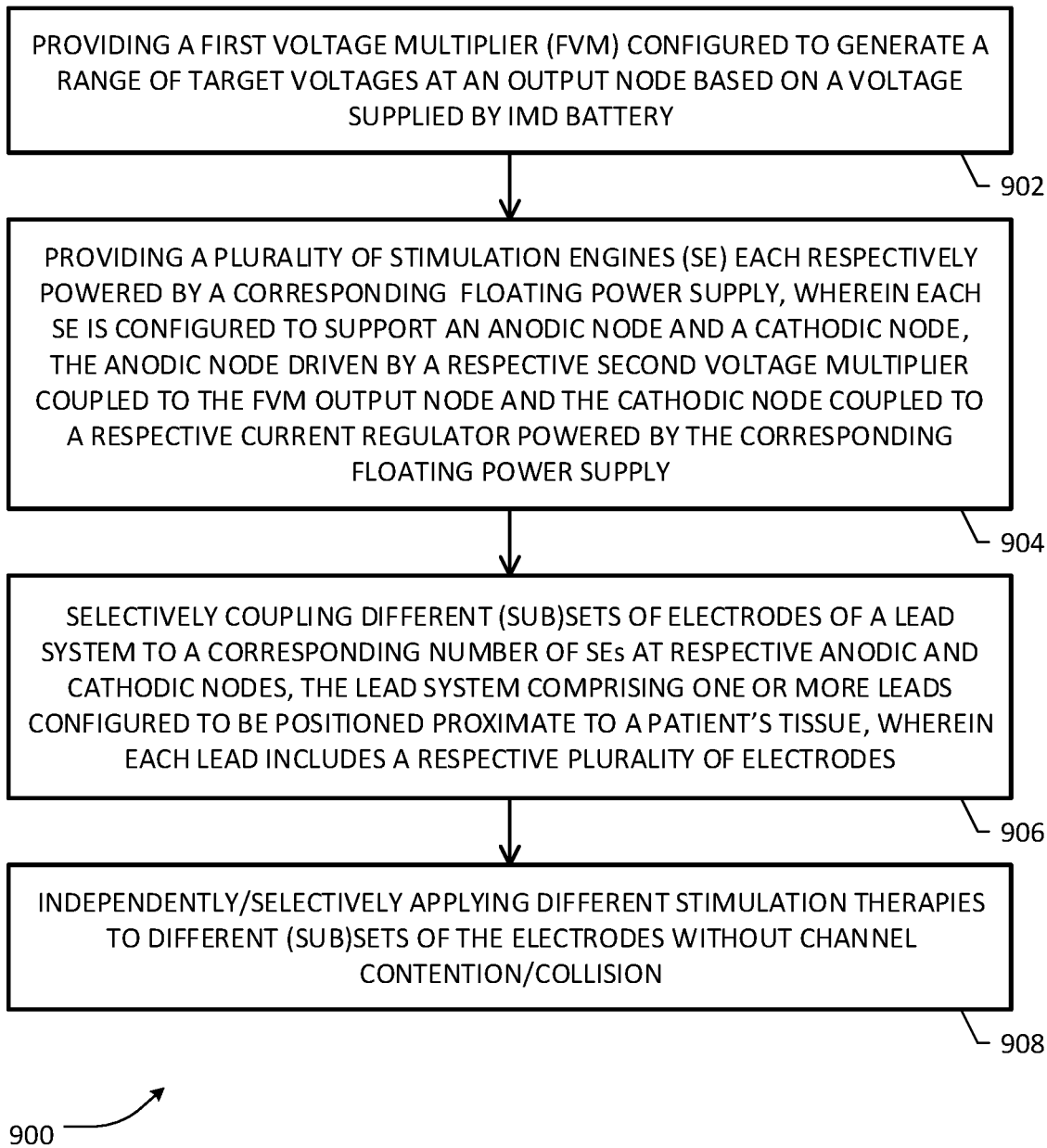
FIG. 9 depicts a flowchart of blocks, steps and/or acts that may be (re)combined in one or more arrangements for facilitating a stimulation therapy method with multiple stimulation engines of a biostimulation system according to some embodiments of the present disclosure.

FIG. 9 depicts a flowchart of blocks, steps and/or acts that may be (re)combined in one or more arrangements for facilitating a stimulation therapy method 900 using multiple stimulation engines of a biostimulation system according to some embodiments of the present disclosure. At block 902, a first voltage multiplier (FVM) configured to generate a range of target voltages at an output node based on a voltage supplied by an IMD battery is provided. At block 904, a plurality of stimulation engines (SE) are provided wherein each SE is respectively powered by a corresponding floating power supply. In one embodiment, each SE is configured to support an anodic node and a cathodic node, the anodic node driven by a respective second voltage multiplier of the SE that is coupled to the FVM output node, wherein the cathodic node is coupled to a respective current regulator powered by the corresponding floating power supply. At block 906, different (sub)sets or portions of electrodes of a lead system may be selectively coupled to or otherwise actuated by a corresponding number of SEs at respective anodic and cathodic nodes, wherein the lead system comprises one or more leads configured to be positioned proximate to a patient's tissue and each lead may includes a respective number or plurality of electrodes. At block 908, different stimulation therapies may be selectively and independently applied to the different (sub)sets of the electrodes without channel contention/collision by the corresponding SEs, wherein each stimulation therapy is provided in accordance with one or more stimset programs.

Based on the foregoing, it should be appreciated that embodiments herein provide a circuit implementation scheme that advantageously allows for multiple SEs to each operate from their own floating power supply, which enables for a wide range of SE voltage multiplier output voltages and stimulation currents to be output at any time by any SE, even simultaneously, without the danger of encountering risks due to stimulation therapy collisions. Example embodiments may be configured to improve compatibility and ease of programming/control of therapy delivery with emerging complex stimulation programs where it would otherwise become increasingly difficult to predict and to avoid therapy collisions, which typically occur in multi-frequency, multi-lead applications such as, e.g., dual brain hemisphere DBS therapies. Accordingly, example embodiments of the present invention may be practiced in a variety of therapy applications including but not limited SCS therapy, DBS therapy, DRG therapy, cochlear stimulation therapy, drug delivery therapy, cardiac pacemaker therapy, cardioverter-defibrillator therapy, cardiac rhythm management (CRM) therapy, an electrophysiology (EP) mapping and radio frequency (RF) ablation therapy, electroconvulsive therapy (ECT), repetitive transcranial (rTMS) magnetic stimulation therapy, and vagal nerve stimulation (VNS) therapy, and the like.

Additional advantages of the present invention may be particularly appreciated in view of the following. In the existing neurostimulator IPG implementations, all stimulation engine circuitry is powered with its negative power supply reference being the negative battery terminal of the IPG. This can prevent multiple stimulation engines from each concurrently outputting optimal stimulation therapies, since only a single voltage multiplier output voltage can be output safely to human tissue at any one time via the anode electrode. In other words, multiple anode electrode voltages that are different (which may be needed to optimize battery current efficiency for each stimulation engine) cannot "collide" as they are simultaneously output to human tissue. Should such a collision or contention occur over a lead system, unintended and largely uncontrolled stimulation currents can flow between the anode electrodes at different voltages. Existing neurostimulator IPGs are unable to avoid those kinds of stimulation "collisions", resulting in at least one non-optimal voltage multiplier setting necessary for the simultaneous delivery of therapy with multiple stimulation engines. In contrast, example embodiments provide a multi-SE arrangement wherein each SE is independently powered, typically from a charge pump capacitor charged to the battery voltage, which allows each SE to independently operate at optimum stimulation efficiency.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, some example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of Integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. An implantable medical device (IMD), comprising:
   a battery;
   a lead system comprising one or more leads configured to be positioned proximate to a patient's tissue, wherein each lead includes a plurality of electrodes;
   a first voltage multiplier configured to generate an adjustable target voltage at an output node based on a voltage supplied by the battery; and
   a plurality of stimulation engines, each respectively including:
      a second voltage multiplier operative to drive an anodic node;
      a current regulator powered by a floating voltage supply, the current regulator coupled to a cathodic node, wherein the second voltage multiplier, the current regulator and the floating voltage supply are commonly referenced to a floating reference node; and
      a selector configured to selectively couple the anodic node and the cathodic node of a respective stimulation engine to a select portion of the electrodes for applying a select stimulation therapy to the patient's tissue according to a stimulation set,
   wherein each anodic node of the plurality of stimulation engines is commonly coupled to the output node of the first voltage multiplier.

2. The IMD as recited in claim 1, wherein each second voltage multiplier of the respective stimulation engine is independently controlled for optimizing a stimulation therapy delivered by the respective stimulation engine to a corresponding select portion of the electrodes.

3. The IMD as recited in claim 2, wherein each current regulator of the respective stimulation engine is configured to independently control cathodic currents drawn from the patient's tissue energized by the corresponding select portion of the electrodes.

4. The IMD as recited in claim 3, wherein each floating power supply of the respective stimulation engine comprises a charge pump capacitor charged to a battery voltage of the IMD.

5. The IMD as recited In claim 4, wherein the stimulation therapy delivered by the respective stimulation engine according to a stimulation set comprises a select set of properties including at least one of a stimulation frequency, a stimulation pulse width, a stimulation pulse amplitude, a discharge method, and phase information.

6. The IMD as recited in claim 4, wherein the stimulation therapy delivered by the respective stimulation engine according to a stimulation set comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial (rTMS) magnetic stimulation therapy, and a vagal nerve stimulation (VNS) therapy.

7. The IMD as recited in claim 1, wherein at least two stimulation engines are configured to concurrently stimulate two corresponding sets of the electrodes without at least one of stimulation delivery collisions and channel contention during delivery of respective stimulation pulses.

8. A stimulation therapy method using an implantable medical device (IMD), the IMD including a battery and a lead system of one or more leads configured to be positioned proximate to a patient's tissue, wherein each lead includes a plurality of electrodes, the method comprising:
   providing a first voltage multiplier configured to generate a range of target voltages at an output node based on a voltage supplied by the battery;
   providing a plurality of stimulation engines (SE), each respectively powered by a corresponding floating power supply, wherein each SE is configured to support an anodic node and a cathodic node, the anodic node driven by a respective second voltage multiplier coupled to the output node of the first voltage multiplier and the cathodic node coupled to a respective current regulator powered by the corresponding floating power supply;
   selectively coupling one or more sets of electrodes of the lead system to a corresponding number of SEs at respective anodic and cathodic nodes; and
   independently applying multiple stimulation therapies to respective sets of the electrodes wherein at least one of stimulation delivery collisions and channel contention between the respective sets of electrodes of the lead system is avoided.

9. The method as recited in claim 8, further comprising independently controlling each second voltage multiplier of a respective stimulation engine for optimizing a stimulation therapy delivered by the respective stimulation engine to a corresponding set of the electrodes.

10. The method as recited in claim 9, further comprising configuring each current regulator of the respective stimulation engine to independently control cathodic currents drawn from the patient's tissue energized by the corresponding set of the electrodes.

11. The method as recited in claim 10, further comprising configuring each floating power supply of the respective stimulation engine as a charge pump capacitor charged to a battery voltage of the IMD.

12. The method as recited in claim 11, wherein a stimulation therapy delivered by the respective stimulation engine comprises a select stimulation set of properties including at least one of a stimulation frequency, a stimulation pulse width, a stimulation pulse amplitude, a discharge method, and phase information.

13. The method as recited in claim 11, wherein a stimulation therapy delivered by the respective stimulation engine according to a stimulation set comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial (rTMS) magnetic stimulation therapy, and a vagal nerve stimulation (VNS) therapy.

14. A therapy system, comprising:
an implantable medical device (IMD) including:
a battery;
a lead system comprising one or more leads configured to be positioned proximate to a patient's tissue, wherein each lead includes a plurality of electrodes;
a first voltage multiplier configured to generate an adjustable target voltage at an output node based on a voltage supplied by the battery; and
a plurality of stimulation engines, each respectively including:
a second voltage multiplier operative to drive an anodic node;
a current regulator powered by a floating voltage supply, the current regulator coupled to a cathodic node, wherein the second voltage multiplier, the current regulator and the floating voltage supply are commonly referenced to a floating reference node; and
a selector configured to selectively couple the anodic node and the cathodic node of a respective stimulation engine to a select portion of the electrodes, wherein each anodic node of the plurality of stimulation engines is commonly coupled to the output node of the first voltage multiplier; and
an external programmer device for independently applying multiple stimulation therapies in a concurrent manner to respective portions of the electrodes by actuating the selector of the IMD according to respective stimulation sets, wherein at least one of stimulation delivery collisions and channel contention between the respective portions of electrodes of the lead system is avoided during concurrent application of the multiple stimulation therapies.

15. The therapy system as recited in claim 14, wherein each second voltage multiplier of the respective stimulation engine is independently controlled for optimizing a stimulation therapy delivered by the respective stimulation engine to a corresponding select portion of the electrodes.

16. The therapy system as recited in claim 15, wherein each current regulator of the respective stimulation engine is configured to independently control cathodic currents drawn from the patient's tissue energized by the corresponding select portion of the electrodes.

17. The therapy system as recited in claim 16, wherein each floating power supply of the respective stimulation engine comprises a charge pump capacitor charged to a battery voltage of the IMD.

18. The therapy system as recited in claim 17, wherein a stimulation therapy delivered by the respective stimulation engine according to a stimulation set comprises a select set of properties including at least one of a stimulation frequency, a stimulation pulse width, a stimulation pulse amplitude, a discharge method, and phase information.

19. The therapy system as recited in claim 17, wherein a stimulation therapy delivered by the respective stimulation engine according to a stimulation set comprises a therapy selected from at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a drug delivery therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial (rTMS) magnetic stimulation therapy, and a vagal nerve stimulation (VNS) therapy.

* * * * *

UNITED STATES PATENT AND TRADEMARK OFFICE
CERTIFICATE OF CORRECTION

PATENT NO. : 11,135,431 B2
APPLICATION NO. : 16/778255
DATED : October 5, 2021
INVENTOR(S) : Daran DeShazo et al.

Page 1 of 1

It is certified that error appears in the above-identified patent and that said Letters Patent is hereby corrected as shown below:

In the Specification

At Column 1, Line number 25, delete "In" and replace with --in--.
At Column 3, Line number 43, delete "In" and replace with --in--.
At Column 6, Line number 46, delete "(Ii)" and replace with --(ii)--.
At Column 8, Line number 27, delete "intemperate" and replace with --interoperate--.
At Column 12, Line number 38, delete "In" and replace with --in--.
At Column 12, Line number 58, delete "In" and replace with --in--.
At Column 14, Line number 10, delete "VM" and replace with --$V_{MAX}$--.
At Column 14, Line number 58, delete "306-1" and replace with --306-i--.
At Column 15, Line number 3, delete "308-" and replace with --308-i--.
At Column 15, Line number 24, delete "306-1" and replace with --306-i--.

In the Claims

At Column 22, Claim number 5, Line number 21, delete "In" and replace with --in--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*